United States Patent [19]

Schomacher

[11] 4,233,981
[45] Nov. 18, 1980

[54] DEVICE FOR CLOSING SEVERED BODY VESSELS

[76] Inventor: Paul H. Schomacher, Braunsbergstrasse 13, 4400 Münster, Fed. Rep. of Germany

[21] Appl. No.: 860,565

[22] Filed: Dec. 14, 1977

[30] Foreign Application Priority Data

Dec. 17, 1976 [DE] Fed. Rep. of Germany ....... 2657255

[51] Int. Cl.³ .............................................. A61B 17/04
[52] U.S. Cl. ................................................ 128/334 R
[58] Field of Search ............... 128/1 R, 334 R, 334 C, 128/335, 335.5, 247, 303, 325, 337, 349, 350, 343, 346, 322, 334; 285/260

[56] References Cited

U.S. PATENT DOCUMENTS

| 2,261,347 | 11/1941 | Di Santo et al. | 302/64 |
| 3,166,072 | 1/1965 | Sullivan | 128/346 X |
| 3,254,650 | 6/1966 | Collito | 128/334 C |
| 3,254,651 | 6/1966 | Collito | 128/334 C |
| 3,258,012 | 6/1966 | Nakayama et al. | 128/334 C |
| 3,316,914 | 5/1967 | Collito | 128/334 C |
| 3,509,883 | 5/1970 | DiBelius | 128/334 C |
| 3,606,888 | 9/1971 | Wilkinson | 128/334 |
| 3,828,764 | 8/1974 | Jones | 128/1 R |
| 4,032,993 | 7/1977 | Coquard | 128/334 R X |
| 4,060,089 | 11/1977 | Noiles | 128/334 C X |

FOREIGN PATENT DOCUMENTS

| 114384 | 12/1941 | Australia | 285/260 |
| 179580 | 6/1962 | Sweden | 285/260 |

Primary Examiner—Edgar S. Burr
Assistant Examiner—James R. Feyrer
Attorney, Agent, or Firm—Fitch, Even, Tabin, Flannery & Welsh

[57] ABSTRACT

A surgical device for joining severed body vessel walls comprises a pair of annular flanges each formed of a plastic material which is compatible with the human body. Pointed pins on one of the flanges are pierced through the vessel walls and inserted into apertures in the other flange to hold and locate the vessel walls. Threaded mounted pins on one of the flanges are inserted through openings in the other of the flanges and threaded nuts are threaded onto the threaded pins to clamp the vessel walls together with a clamping pressure. The clamping pressure may be adjusted by turning the threaded nuts. Clamping pressure may be relieved to prevent a necrotic condition by turning the nuts in the turn off direction.

2 Claims, 6 Drawing Figures

DEVICE FOR CLOSING SEVERED BODY VESSELS

The present invention relates to a device for closing severed body vessels, especially blood vessels, comprising essentially a pair of, preferably annular, flange portions formed of a plastics material that is compatible to the body, said flange portions being positioned with their planar faces in opposed relationship and interconnected through holding pins in their closing position, such that parts of the vessels walls come to lie between said interconnected flange portions.

It is known to join body vessels by means of direct vascular sutures. In such case, the whipped, continuous suture is used for the restoration of the flow path. In general, suturing of larger arteria does not present any difficulty. In contrast, small vessels having a diameter of less than 5 mm cannot always be joined without causing constriction of the lumen by the suture per se, in spite of highly advanced suturing methods. Such constriction then results in stenosis or in thrombotic clogging of the suture area. Therefore, it has already been proposed and disclosed to close fine vessels of this kind by means of a device designed by Nakayama ("Bruns Beiträge zur klin. Chirurgie", volume 214, p. 152, 1967). The Nakayama device comprises essentially a pair of annular flange portions being provided with six extremely fine lugs or pins each, said pins opposing six mating riveting holes. The vessel wall is fixed to the pins with eventration. The rings are grasped by means of ring retainer pliers in a manner that such rings—when the ends of the vessel have been drawn onto the rings on either side—may be pressed against each other and riveted together. In this way, one vascular intima or innermost coat of the vessel contacts the opposite vascular intima. The lumen is not constricted, and foreign matter or rough portions do not exist. The "clearance" is defined by the dimensions of the rings. However attachment of the Nakayama rings requires the provision of a specific device of pliers-like configuration which cannot be employed in regions which are difficult to access, e.g. in the hollow of the knee.

The device designed by Nakayama has already been used with success. However, it has been found that the device, due to the fixed, predetermined position and length of the pins, cannot be adequately conformed to different thicknesses of the eventrated vascular walls. Furthermore, it might happen in the case of extremely thin vascular walls that these walls are not retained between the conventional rings with a sufficiently tight grip; on the other hand, in the case of relatively thick vascular walls there exists the danger that the walls are pressed against each other with too great a force so as to be liable to be devitalized, and this might result in thrombosis and in causing aneurism.

For improving the conventional apparatus, it is therefore the object of the present invention to design this device in a way that the pressure exerted by the flange portions (rings) may be selected so that the connection is sufficiently tight in any case, while such connection may be loosened or released so as to prevent the vascular walls from becoming necrotic (devitalized). Furthermore, the improved device should be designed in a fashion that a special instrument of the abovementioned type may be omitted.

These primary objects of the invention are solved by a device in which the holding pins are at least partially provided with threads. These threads may be tightened with the aid of a nut to such degree that the surgeon can decide what degree of pressure exerted upon the vascular walls is still tolerable. If the joint is too weak, the nuts may be tightened with somewhat greater force. If it is found in the course of the surgical operation that the vessels tend to become necrotic, the nuts may be loosened. A particular advantage is the fact that the novel device, by adjusting the force of contact, enables the surgeon to exert relatively higher loads upon the vascular walls. This feature is of particular advantage if vascular prosthetic parts are to be joined by means of the flanges. On the whole, it is found that flange portions having such a lumen (inner diameter) may be prepared which conform themselves to various diameters of vessels. Reference may be made to the fact that the term "body vessels" is intended to include particularly blood vessels. However, the novel device may used also for closing other hollow organs, such as e.g. bile-ducts, ureters or wide lymphatic vessels and the like.

In particular, it is proposed that each holding pin has one end thereof securely anchored in one of the flange portions, while the other flange portion is provided with bores in the flat faces thereof, with the threaded pins of the facing flange portion being adapted to be passed through such bores.

It is of particular advantage that the novel device, due to its principally higher loading capacity, may be formed also with such configuration that one of said flange portions includes an inwardly stepped insertion surface into which the opposite flange portion may be inserted in closing the device. This arrangement offers the advantage that the vascular walls in the case of laterally branching vascular elements, namely so-called end-to-side anastomosis, my be inserted in a manner so as not to reduce the lumen. It is especially in operations of this kind that the treated vessels are readily subject to thrombosis.

It is likewise possible to construct one of the flange portions as a closure (cover) plate. In this case, too, the inwardly stepped insertion surface is advantageous in so far as obstructions to flow are substantially completely avoided.

Additionally, it is possible to provide vascular prosthetic parts with the flange portions according to the invention as peripheral terminal members. It is particularly these parts that require a short period of (surgical) operation; on the other hand, the stresses exerted upon the natural vessels involved are frequently quite high. In such case, too, the proposed principle proves to be particularly progressive.

It has been found in surgical test operations to be advantageous when the flange portions are formed of an absorbable plastics material. As the parts of body vessels disposed between the flange portions are not necrotic, these parts grow together after a short time. Hereby, the flange portions then become unnecessary. In order to avoid another surgical operation, it is preferable to cause these flange portions to be "dissolved". The holding pins, if made of a noble metal, are left at the point of operation.

In the following, the device according to the invention is explained in greater detail by referring to the enclosed drawing illustrating preferred embodiments. In the FIGS:

Figure 1:
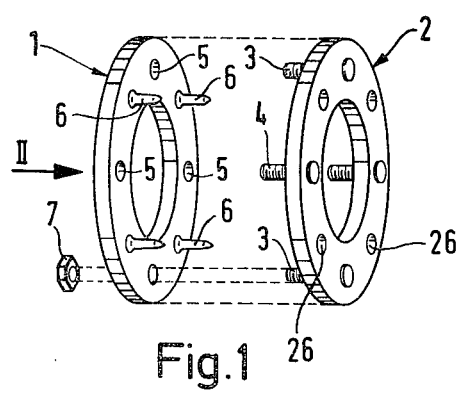
FIG. 1 shows the two elements of the device on enlarged scale.

FIG. 1 shows the device for closing severed body vessels on a slightly enlarged scale. This device comprises essentially a pair of preferably annular flange portions 1, 2 made of a compatible plastics material, e.g. PTFE. It is also possible to prepare the rings of the device from a noble metal or from an absorbable plastics material, such as is known per se in the vessel surgery art. For instance, poly-glycosamides which are decomposed by hydrolysis are suitable for this purpose.

The size of the flange portions may vary. This size depends on the contemplated field of use. For example, the rings may be formed with an inside diameter of about 4 mm and an outside diameter of about 10 mm. The thickness may be e.g. 2 mm. Of course, these dimensions should be taken as examples only. As the device according to the invention also allows to close even larger vessels, flange portions of a correspondingly adapted size must be used to this end.

One flange portion 2 has the ends of pins 3, 4 embedded therein, for instance by a melting or fusing step, such that these pins protrude perpendicularly from the flat face of the respective flange portion. Pins 3, 4 are threaded, and these pins are adapted to be passed through corresponding holes or bores 5 of flange portion 1. On the opposite side, the threaded pins provided with nuts 7 reacting against the outer side of flange portion 1 to thereby press flange portion 2 against flange portion 1 upon tightening the nuts. Normally, only four or six pins of this type are provided such that the device may be uniformly tightened on either side thereof. However, it is possible to do with only a pair of opposed threaded pins. Turning and tightening of the screws (threaded pins) is effected with the aid of well-known precision mechanical tools as are employed in the watchmaking art. Flange portion 1 is likewise provided with pins 6 which are not threaded, however, but which are merely passed through opposed bores 26 so as to provide for exact alignment. Besides, pins 6 act to hold the eventrated vessel walls.

Of course, it is also possible to provide both flange portions, in the place of fixed pins, with holes or bores, and to insert headed screws through such bores, which screws are then tightened by mating nuts.

Figure 3:
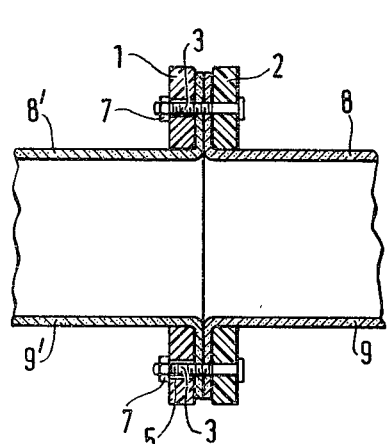
FIG. 3 illustrates the device in its joining state.

FIG. 3 illustrates the components of the device in situ. The walls 8, 9; 8', 9' of a blood vessel, are eventrated, i.e. laid around the flat faces of flange portions 1, 2. In this step, the vascular walls are simultaneously penetrated by pins 3, 6. Thereupon, flange portions 1, 2 are shifted towards each other, with the pins 3, 4, 6 passing through bores 5, 26. Then, the threaded pins are tightened by using nuts made ready in advance. Parts of the vascular wall are then positioned between flange portions 1, 2. Depending on the thickness and consistences of the vascular wall parts, the nuts are thereafter thightened to such extent that the two wall parts, on the one hand, are tightly pressed against each other with their inner sides, while, on the other hand, such pressure contact must not be so tight that the tissues might be devitalized. Evidently, this operation requires some skill or some experience from the operator. It shows that the pressed-together vascular wall portions in almost every instance grow together after some period of time to form a cicatrice free from stenosis and covered without interruption by the intima (innermost coat) of the vessel.

Figure 4:
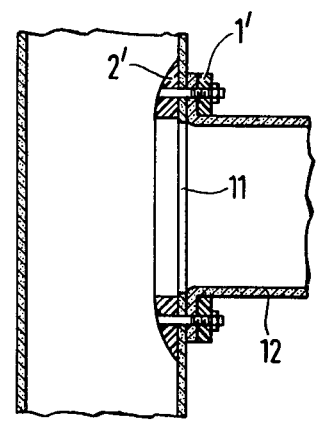
FIG. 4 shows another embodiment of the present device for an end-to-side joint.

FIG. 4 shows an end-to-side anastomosis. Conventionally, a surgical operation of this kind is difficult to perform without causing thrombosis and stenosis. On the other hand, the device according to the invention provides for substantially easier performance of such surgical operation. To this end, initially a section of the vessel, e.g. of an artery, is made. this section which results, for example, in an approximately oval incision 11, may then be backed up by a flange portion 2' being provided with threaded pins which penetrate the vascular wall. Thereupon, a mating portion (flange portion 1') already carrying the eventrated end of a vessel 12, is pressed upon the flange portion 2' backing the vascular wall from the opposite side. The ends of the threaded pins hereby passed through the holes or bores provided in flange portion 1'. Then, the threaded pins are tightened (by means of nuts), whereby the contact pressure, again, may be adjusted as required. This operative technique can be applied by using the device according to the invention even to arteriosclerotic veins or vessels which are normally very difficult to suture and which cannot be joined in practice with an end-to-side joint by using the device designed by Nakayama.

Figure 2:
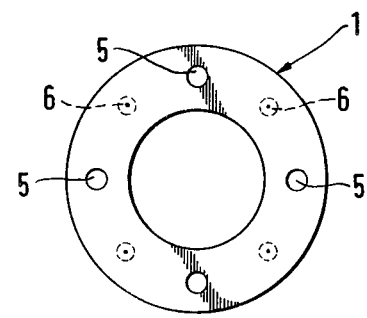
FIG. 2 shows one of the flange portions of the device in plan view.
Figure 5:
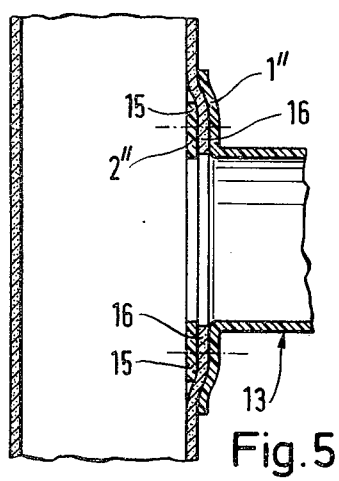
FIG. 5 illustrates a still further embodiment of the present device in combination with a vascular prosthetic part.

Finally, reference may be made to FIG. 5 showing a vascular prosthesis 13 having one end thereof provided with a flange portion 1". This flange portion 1" includes an inwardly stepped insertion surface 15. Conforming to this stepped surface, the opposing side carrying an interposed body tissue part 16, is provided with a flange portion 2" carrying threaded pins which, in turn, may be passed through corresponding holes or bores in portion 1". This structure provides the advantage that the prosthesis 13, owing to the stepped insertion surface, may be attached in such a manner that substantially no restriction of the lumen is involved, namely that the fluid flowing within the constrictions or aneurisma occur in the artificial closure of vessels, which might result in thrombotic phenomena. Of course, it is possible to use the stepped insertion surface according to FIG. 5 also in a flange portion without any vascular prosthesis joined thereto. Furthermore, a "closure member" or a closure plate may be used instead of the vascular prosthesis, which member or plate allows to cover a fissure in a vessel in easy manner. This member will look like the part of FIG. 2, but without the central bore.

In the case of large vessels (aorta), a closure cap may have the edges thereof formed of rigid plastics materials while the center portion thereof is made of a softly elastic material capable of following the movement of the respective vessel. As surgical test operations with animals have shown, the joint may be applied both to arterio-arterial joints, to arterio-venous joints and to the interpolation of venous implantants. The latter example applies to replacing vessel sections by prostheses.

Evidently, it is possible to provide the flange portions with rounded shoulders, milled-in pads or bonded soft plastics material to thereby avoid injuries and pressure areas. These feature are not shown in the drawing.

Figure 6:
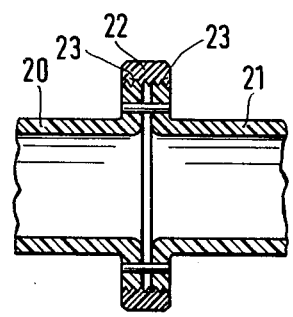
FIG. 6 shows an extension joint for vascular prosthetic parts according to the invention.

FIG. 6 illustrates another advantageous mode of using the device according to the invention. When vascular prostheses are implanted, the requisite length of such parts cannot always be estimated precisely at the start of the the surgical operation, even if—in a manner known per se—longitudinally elastic prosthetic parts are employed. However, the implanted prosthetic part by no means must be too long. Accordingly, the operating surgeon would intitially implant a prosthesis 20 of a predetermined, somewhat too short tubular length. The free end of this prosthetic part may then have attached thereto a corresponding further prosthetic part 21 provided with a flanged end according to the invention, with such flanged ends, in turn, being connected to each other by a threaded connection. Preferably, such threaded connection is made by means of a screw cap (union nut) 22 screwed onto threads 23 formed on the outer periphery of the flange. Accordingly, it is suggested that at least the outer peripheries of the flanges be provided with threads enabling the use of a screw cap.

What I claim is:

1. A surgical device for closing severed body vessel walls comprising:
   a pair of annular flanges each formed of a material compatible to a human body,
   said flanges being positionable to having their planar faces in opposed relationship with vessel walls disposed between said flanges,
   pointed pins anchored to one of said flanges and extending through openings in the other flange and piercing the vessel walls between said flanges and retaining their pointed ends,
   threaded holding pins mounted on one of said flanges and having threaded portions extending through aligned apertures in the other of said flanges,
   and threaded fasteners for threading onto said threaded holding pins to hold said flanges and said pointed pins against separation, said threaded fasteners being turned in one direction on said threaded holding pins to various locations depending on the thickness of the vessel walls, said threaded fasteners being turnable in a direction opposite to said one direction to reduce the clamping pressure on the vessel walls to prevent a necrotic condition.

2. A device in accordance with claim 1 further comprising an inwardly stepped insertion surface on one of said flanges.

* * * * *